US011260063B2

(12) United States Patent
Yuhas

(10) Patent No.: US 11,260,063 B2
(45) Date of Patent: **\*Mar. 1, 2022**

(54) METHOD AND COMPOSITIONS FOR TREATING PSORIASIS

(71) Applicant: Chem-Cure Associates LLC, New York, NY (US)

(72) Inventor: Edward Richard Yuhas, Yonkers, NY (US)

(73) Assignee: Chem-Cure Associates LLC, New York, NY (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/717,114

(22) Filed: Dec. 17, 2019

(65) Prior Publication Data

US 2020/0129529 A1   Apr. 30, 2020

Related U.S. Application Data

(63) Continuation of application No. 16/156,820, filed on Oct. 10, 2018, now Pat. No. 10,525,065, which is a continuation of application No. 15/639,886, filed on Jun. 30, 2017, now Pat. No. 10,124,013, which is a continuation of application No. 13/655,161, filed on Oct. 18, 2012, now Pat. No. 9,717,741, which is a continuation of application No. PCT/US2012/059701, filed on Oct. 11, 2012.

(51) Int. Cl.
*A61K 31/575* (2006.01)
*A61K 9/00* (2006.01)
*A61K 47/12* (2006.01)
*A61K 47/14* (2017.01)
*A61K 9/12* (2006.01)
*A61P 17/06* (2006.01)
*A61K 9/06* (2006.01)
*A61Q 19/00* (2006.01)

(52) U.S. Cl.
CPC .......... *A61K 31/575* (2013.01); *A61K 9/0014* (2013.01); *A61K 9/06* (2013.01); *A61K 9/12* (2013.01); *A61K 47/12* (2013.01); *A61K 47/14* (2013.01); *A61P 17/06* (2018.01); *A61Q 19/00* (2013.01)

(58) Field of Classification Search
CPC .............................. A61K 31/575; A61Q 19/00
See application file for complete search history.

(56) References Cited

U.S. PATENT DOCUMENTS

| | | |
|---|---|---|
| 2,798,053 A | 7/1957 | Brown |
| 2,909,462 A | 10/1959 | Warfield et al. |
| 4,138,416 A | 2/1979 | Koresawa et al. |
| 4,207,893 A | 6/1980 | Michaels |
| 4,327,725 A | 5/1982 | Cortese et al. |
| 4,743,597 A | 5/1988 | Javitt et al. |
| 4,760,096 A | 7/1988 | Sakai et al. |
| 4,915,949 A | 4/1990 | Wong et al. |
| 5,034,228 A | 7/1991 | Meybeck et al. |
| 5,051,260 A | 9/1991 | Chess et al. |
| 5,179,086 A | 1/1993 | Flender |
| 5,429,816 A | 7/1995 | Hofrichter et al. |
| 5,552,136 A | 9/1996 | Motley |
| 5,614,215 A | 3/1997 | Ribier et al. |
| 5,643,588 A | 7/1997 | Roe et al. |
| 5,811,083 A | 9/1998 | Pelle et al. |
| 5,834,016 A | 11/1998 | Naeff et al. |
| 5,945,409 A | 8/1999 | Crandall |
| 6,153,209 A | 11/2000 | Vega et al. |
| 6,309,656 B1 | 10/2001 | Pugliese et al. |
| 6,316,428 B1 | 11/2001 | Crandall |
| 6,361,806 B1 | 3/2002 | Allen |
| 6,419,954 B1 | 7/2002 | Chu et al. |
| 6,420,578 B1 | 7/2002 | Cawthorne et al. |
| 6,613,866 B2 | 9/2003 | Zofchak et al. |
| 6,830,758 B2 | 12/2004 | Nichols et al. |
| 6,946,120 B2 | 9/2005 | So et al. |
| 7,368,122 B1 | 5/2008 | Dow et al. |
| 7,381,417 B2 | 6/2008 | Gamez-Garcia |
| 7,449,613 B2 | 11/2008 | Klofta et al. |
| 9,717,741 B2 * | 8/2017 | Yuhas ................... A61K 47/14 |
| 10,124,013 B2 * | 11/2018 | Yuhas ................... A61K 9/122 |
| 10,525,065 B2 * | 1/2020 | Yuhas ................... A61P 17/06 |
| 2002/0182260 A1 | 12/2002 | Mak et al. |
| 2006/0172022 A1 | 8/2006 | Szanzer |
| 2006/0275233 A1 | 12/2006 | Fishman et al. |
| 2007/0110685 A1 | 5/2007 | Auspitz et al. |
| 2007/0196459 A1 | 8/2007 | Zhang et al. |
| 2007/0269379 A1 | 11/2007 | Mitragotri et al. |
| 2011/0217248 A1 | 9/2011 | Spann-Wade et al. |

FOREIGN PATENT DOCUMENTS

| | | |
|---|---|---|
| GB | 1532209 | 11/1978 |
| JP | S60-16927 | 1/1985 |
| JP | S62-242614 | 10/1987 |
| JP | H06-234644 | 8/1994 |

(Continued)

OTHER PUBLICATIONS

Lotion Crafter LLC, Super Sterol Liquid, 2 pages, Jan. 1, 2012.
Lotion Crafter, Super Sterol Liquid MSDS, 2 pages, Jan. 19, 2008.
Croda, Super Sterol Liquid, 13 pages, May 25, 2006.
Ajinmoto, CFTA International Buyer's Guide (electronic), 1 page, Jun. 30, 2004.
(Author unknown), List of Animal-Derived Ingredients Used in Cosmetics, 1 page, Jan. 3, 2002.
Croda, Super Sterol Ester: C10-C30 Cholesterol/Lanosterol Esters, 2 pages, Feb. 2000.
Croda, Super Sterol Ester product details, 2 pages, 2012.
Croda, "A Soul Mate For the Skin . . . Super Sterol Liquid", 2006, 2 pages.
Croda, Safety Data Sheet for Super Sterol(TM) Liquid-LQ-(JP), Sep. 12, 2011, 8 pages.

(Continued)

*Primary Examiner* — Gina C Justice

(74) *Attorney, Agent, or Firm* — Florek & Endres PLLC; Martin Endres

(57) ABSTRACT

A topical composition useful for treating psoriasis and other skin disorders.

17 Claims, No Drawings

(56) References Cited

FOREIGN PATENT DOCUMENTS

| | | |
|---|---|---|
| JP | H09-227375 | 9/1997 |
| JP | 2005-535614 | 11/2005 |
| RU | 2091065 | 9/1997 |
| RU | 2093190 | 12/1998 |
| RU | 2123334 | 12/1998 |
| WO | 2004000242 | 12/2003 |

OTHER PUBLICATIONS

Wiftcraftymonkey Blogspot, "Lipstick: Croda's Super Sterol Lipstick Base", Sep. 8, 2009, 2 pages.

Croda, Beta-Hydroxy Acid Cream with CROAFOS(TM) CES, Mar. 26, 2010, 1 page.

Croda, Body Smoother, Mar. 26, 2010, 1 page.

Croda, Conditioner for Soft Strong Shiny Hair, Mar. 26, 2010, 1 page.

Croda, Emollient Hydrating Cream for Mature Skin, Jan. 26, 2010, 1 page.

Croda, Hair Strengthening Creme Rinse with Keravis(TM) and Incroquat(TM) Behenyl TMS-50, Dec. 8, 2010, 1 page.

Croda, Hand & Nail Lotion, Aug. 23, 2010, 1 page.

Croda, Hydrosolanum(TM) PE Moisturizing Conditioning Cream, Jan. 27, 2010, 1 page.

Croda, Maximum Shine, Long-Wearing Lipstick, Jan. 29, 2010, 2 pages.

Croda, Milky Moisturizing Body Spray, Jan. 29, 2010, 1 page.

Croda, O/W Smoothing Spray, Dec. 22, 2009, 1 page.

Croda, Shine-On Lipstick with Crodamol(TM) STS, Apr. 12, 2010, 2 pages.

Croda, Skin Brightening Cream with Lumiskin(TM), Apr. 9, 2010, 2 pages.

Croda, Smile for a While Lipstick, Nov. 2, 2011, 1 page.

Croda, Smile for a While Lipstick, Feb. 7, 2012, 1 page.

Croda, Super Moisturizing Lipstick, Feb. 2, 2010, 1 page.

Croda, Formulation Details for Beta-Hydroxy Acid Cream with Crodafox CES-SC-301-3, 1 page, date unknown but Applicants believe it is from prior to the application's Oct. 11, 2012 priority date.

Croda, Formulation Details for Body Smoother—SC-331-3, 1 page, date unknown but Applicants believe it is from prior to the application's Oct. 11, 2012 priority date.

Croda, Formulation Details for Conditioner for Soft Strong Shiny Hair—HP-266-3, 1 page, date unknown but Applicants believe it is from prior to the application's Oct. 11, 2012 priority date.

Croda, Formulation Details for Emollient Hydrating Cream for Mature Skin—SC-335-2, 1 page, date unknown but Applicants believe it is from prior to the application's Oct. 11, 2012 priority date.

Croda, Formulation Details for Hair Strengthening Creme Rinse w Keravis & Incroquat Behenyl TMS-50—HP-233-2, 1 page, date unknown but Applicants believe it is from prior to the application's Oct. 11, 2012 priority date.

Croda, Formulation Details for Hand & Nail Lotion—SC-209-4, 1 page, date unknown but Applicants believe it is from prior to the application's Oct. 11, 2012 priority date.

Croda, Formulation Details for High Luster Lip Gloss—MU 87-1, 1 page, date unknown but Applicants believe it is from prior to the application's Oct. 11, 2012 priority date.

Croda, Formulation Details for Hydrosolanum PE Moisturizing Conditioning Creme—SC-311-2, 1 page, date unknown but Applicants believe it is from prior to the application's Oct. 11, 2012 priority date.

Croda, Formulation Details for Intensive Repair Hand Cream with Super Sterol Liquid—SC-364-3, 1 page, date unknown but Applicants believe it is from prior to the application's Oct. 11, 2012 priority date.

Croda, Formulation Details for Lip Balm with Maxi-Lip—MU-90-1, 1 page, date unknown but Applicants believe it is from prior to the application's Oct. 11, 2012 priority date.

Croda, Formulation Details for Lip Cream with Super Sterol Liquid and Crodamol STS—MU-82-3, 1 page, date unknown but Applicants believe it is from prior to the application's Oct. 11, 2012 priority date.

Croda, Formulation Details for Maximum Shine, Long-Wearing Lipstick, MU-86-1, 1 page, date unknown but Applicants believe it is from prior to the application's Oct. 11, 2012 priority date.

Croda, Formulation Details for Milky Moisturizing Body Spray—SC-309-4, 1 page, date unknown but Applicants believe it is from prior to the application's Oct. 11, 2012 priority date.

Croda, Formulation Details for O/W Smoothing Spray—SC-532, 1 page, date unknown but Applicants believe it is from prior to the application's Oct. 11, 2012 priority date.

Croda, Formulation Details for Revitalizing Night Cream—SC-571-1, 1 page, date unknown but Applicants believe it is from prior to the application's Oct. 11, 2012 priority date.

Croda, Formulation Details for Shine-On Lipstick with Crodamol STS—MU-77-3, 1 page, date unknown but Applicants believe it is from prior to the application's Oct. 11, 2012 priority date.

Croda, Formulation Details for Skin Brightening Cream with Lumiskin—SC-381-3, 1 page, date unknown but Applicants believe it is from prior to the application's Oct. 11, 2012 priority date.

Croda, Formulation Details for Smile for Awhile Lipstick—MU-97, 1 page, date unknown but Applicants believe it is from prior to the application's Oct. 11, 2012 priority date.

Croda, Formulation Details for Smile for Awhile Lipstick—MU-97-1, 1 page, date unknown but Applicants believe it is from prior to the application's Oct. 11, 2012 priority date.

Croda, Formulation Details for Super Moisturizing Lipstick—MU-068-2, 1 page, date unknown but Applicants believe it is from prior to the application's Oct. 11, 2012 priority date.

Croda, "Biomimetics at its Best . . . Lanolin from Croda", 6 pages, date unknown but Applicants believe it is from prior to the application's Oct. 11, 2012 priority date.

Croda, "Blue: Low Energy Pathways to Green", Blue Guide, North American Edition, 27 pages, date unknown but Applicants believe it is from prior to the application's Oct. 11, 2012 priority date.

Croda, Hair Care—Blue: Low Energy Pathways to Green, 13 pages, date unknown but Applicants believe it is from prior to the application's Oct. 11, 2012 priority date.

Croda, "Color Science for the World of Beauty", 12 pages, date unknown but Applicants believe it is from prior to the application's Oct. 11, 2012 priority date.

Croda, Cosmetic Chemistry Chronicle, The Monthly Guide to Croda Beauty Ingredients, 5 pages, Apr. 2011.

Croda, Cosmetic Chemistry Chronicle, The Monthly Guide to Croda Beauty Ingredients, 4 pages, Oct. 2010.

Croda, The HLB System, Croda's Time-Saving Guide to Emulsifier Selection, 28 pages, date unknown but belief that prior to the application's Oct. 11, 2012 priority date.

Dow Chemical Company, Dowicil 200 Preservative, 16 pages, May 1999.

Alzo International Inc., Polyderm Polyurethanes, 15 pages, date unknown but Applicants believe it is from prior to the Oct. 11, 2012 priority date.

Author Unknown, An Introduction to Aerosol Propellants, 52 pages, date unknown but Applicants believe it is from prior to the Oct. 11, 2012 priority date.

Croda, Glycerox 767, 2 pages, date unknown but Applicants believe it is from prior to the Oct. 11, 2012 priority date.

Goodman & Gilman, The Pharmacological Basis of Therapeutics, 9th ed. 1996, pp. 331-347, 1456-1483 and 1591-1613.

Lotioncrafter and Croda, Polawax NF, 5 pages, date unknown but Applicants believe it is from prior to the Oct. 11, 2012 priority date.

Croda, Specialty Ingredients for Personal Care, Nov. 2005, 62 pages.

Croda, Super Sterol Ester, 2 pages, date unknown but Applicants believe it is from prior to the Oct. 11, 2012 priority date.

Croda, "A Soul Mate for the Skin", 2 pages, date unknown but Applicants believe it is from prior to the Oct. 11, 2012 priority date.

(56) References Cited

OTHER PUBLICATIONS

Author Unknown, "Psoriacure", 1 page, date unknown but Applicants believe it is from prior to the Oct. 11, 2012 priority date.
Croda, Material Safety Data Sheet for Super Sterol Liquid, Dec. 9, 2005. 4 pages.
msn.com, The Three Stages of Psoriasis Treatment, retrieved Apr. 23, 2012, 10 pages.
National Psoriasis Foundation, "Getting to Know" 4 pages, date unknown but Applicants believe it is from prior to Oct. 11, 2012 priority date.
psoriasisconnect.com, "Psoriasis Connections", retrieved Oct. 28, 2006, 6 pages.
National Psoriasis Foundation, "Learn: Treating Psoriasis", retrieved Dec. 28, 2011, 9 pages.
National Psoriasis Foundation, "Psoriasis Treatment: Topicals", retrieved Jul. 7, 2005, 1 page.
National Psoriasis Foundation, "Topical Treatments for Psoriasis, Including Steroids", pp. 1-20, 2009.
Ed Anderson, "Psoriasis Hall of Pshame", (c) 1998-2004, 21 pages.
David B. Troy (ed.), Remington: The Science and Practice of Pharmacy, 21s ed., 2006, Chapter 50 on Aerosols by J.J. Sciarra and C.J. Sciarra, pp. 1000-1017.
Kiliniskaya, A. International Search Report in PCT/US2012/059701, 3 pages, Jul. 4, 2013, Federal Institute of Industrial Property, Moscow, Russia.
Kiliniskaya, A., Written Opinion of the International Searching Authority in PCT/US2012/059701, 4 pages, Jul. 4, 2013, Federal Institute of Industrial Property, Moscow, Russia.
Bos et al., Topical treatments in psoriasis: today and tomorrow, Clinics in Dermatology, J.B. Lippincott, Philadelphia, 2008, 26(5): 432-437.
Fluhr et al., Emollients, moisturizers, and keratolytic agents in psoriasis, Clinics in Dermatology, J.B. Lippincott, Philadelphia, 2008, 26(4): 380-386.
Croda Inc., Super Sterol Ester, 1994, Retrieved from http://crodausa.com/datasheets/Super_Sterol_Ester_DS-63.pdf.
Croda Inc., Super Sterol Liquid. Skin Repair, Conditioning and Moisturization, 2006, Retrieved from https://www.lotioncrafter.com/reference/tech_data_super_sterol_liquid.pdf.
Schmidt et al. Cholesterol and Cholesteryl Ester Content in Normal and Pathologic Scale, J. Investig. Dermatol., 1977, vol. 68, No. 4, pp. 206-209.

* cited by examiner

METHOD AND COMPOSITIONS FOR TREATING PSORIASIS

This application is a continuation of U.S. patent application Ser. No. 16/156,820 filed Oct. 10, 2018 which is a continuation of U.S. patent application Ser. No. 15/639,886 filed Jun. 30, 2017, now U.S. Pat. No. 10,124,013, which is a continuation of U.S. patent application Ser. No. 13/655,161, filed Oct. 18, 2012, now U.S. Pat. No. 9,717,741, which is a continuation of International Patent Application No. PCT/US12/59701, filed on Oct. 11, 2012, the contents of all are hereby incorporated by reference in their entireties into the present application.

TECHNICAL FIELD OF THE INVENTION

The present invention relates to a method and compositions for treating psoriasis and other similar skin disorders such as eczema, sunburn, and wound and scar care. The method comprises the topical administration of a composition comprising a sterol ester.

BACKGROUND OF THE INVENTION

Psoriasis is a skin disease that results when skin cells reproduce at a faster than normal rate. Psoriasis produces red patches, sometimes referred to as plaques, and dry grayish-white or silvery scales on a patient's skin.

A number of different treatments are currently employed to treat psoriasis outbreaks. One of the more common treatments is the topical application of corticosteroids to the affected area to reduce the inflammation. The patient may develop a resistance over time to corticosteroids and therefore their use is often limited.

Other common treatments involve the topical application of anthralin, also known as dithranol, the topical application of a vitamin D such as calcipotriene or calcitriol, or the topical application of a vitamin A such as tazarotene. It is believed that anthralin, vitamin D and vitamin A slow the patient's production of new skin cells. Anthralin can stain a patient's skin or clothing and does not work well on very active psoriasis outbreaks. The topical applications of vitamins D and/or A may make a patient sensitive to sun light.

Coal tar has also been used to treat psoriasis. The coal tar can be applied directly to the affected area or it can be added to bath water. Although helpful, coal tar has a strong and unpleasant odor.

The topical application of salicylic acid has also been employed with some psoriasis patients. Salicylic acid is believed to function as a peeling agent that will cause the outer layer of skin to shed. Salicylic acid may cause irritation and/or hair loss if left on the skin for extended periods of time.

Some psoriasis patients have also used ultraviolet light to treat psoriasis. The ultraviolet light can involve the use of controlled amounts of natural sunlight on the exposed area or artificial sources directed to the affected area.

Other patients have combined oral administration of psoralen, also known as psoralene, with ultraviolet light treatments.

Still other psoriasis patients have used orally administered retinoids, i.e., very concentrated forms of vitamin A, or drugs that slow down the patient's immune system such as methotrexate or cyclosporine.

Psoriasis patients are also advised to keep the skin moist by using moisturizing creams, lotions and soaps to help reduce the redness and itching associated with the psoriasis outbreaks or to use bath oils and salts.

Although there are many potential treatment options for psoriasis, none of the above mentioned methods are 100% successful or without adverse potentials.

It is an object of the present invention to provide a method for treating psoriasis and to provide compositions that are useful in treating psoriasis without unpleasant odors or irritation to the patient's skin.

SUMMARY OF THE INVENTION

The present invention accomplishes the above objectives and others by providing a method of treating psoriasis comprising the topical application of a composition comprising a sterol ester, preferably $C_{10}$-$C_{30}$ carboxylic acid sterol esters, to the psoriatic area of a patient. The application of the composition will occur as needed but should occur at least once daily and preferably immediately or shortly after, i.e., within 5, 10 or 15 minutes, washing and drying the affected area. The application of the composition to the psoriatic area should continue periodically until the psoriasis plaques and scales have been removed.

The composition may be applied to the psoriatic area in an unoccluded or occluded manner. In one embodiment of the invention the composition should remain in contact with the psoriatic area for at least 20 minutes or longer, preferably at least 30 minutes or longer.

The composition may be a gel, cream, paste, lotion, ointment, salve, serum, spray, aerosol, mousse or foam. Preferably the composition is a serum, aerosol, mousse or foam.

In one embodiment of the present invention, the composition should comprise 25% or more of a sterol ester, preferably a $C_{10}$-$C_{30}$ carboxylic acid sterol ester, based upon the total weight of the composition less solvent, preferably 30% or more based upon the total weight of the composition less solvent and most preferably 40% or more based upon the total weight of the composition less solvent.

In an alternative embodiment of the present invention, the composition of the present invention will comprises a mixture of a sterol ester, preferably a $C_{10}$-$C_{30}$ carboxylic acid sterol ester, and a penetration enhancer.

It is also believed that the compositions of the present invention are also useful in treating skin disorders and afflictions such as eczema, sunburn, and wound and scar care

DETAILED DESCRIPTION OF THE INVENTION

As used herein, the term "psoriasis" refers to a dermatological condition that is believed to be caused by the patient's body producing too many skin cells. The condition is associated with red patches, thick white/silvery scales and often swelling on the patient's skin, typically on the arms, scalp, ears and pubic area. It is believed that psoriasis cannot be cured but may be treated.

As used herein, the terms "treat" or "treating" refers to providing relief of one or more of the conditions associated with psoriasis or diminishing or lessening any one or more of the conditions associated with psoriasis.

As used herein, the terms "enhancement," "penetration enhancement" and "permeation enhancement" mean an increase in the permeability of a biological membrane (e.g., skin or mucosa) to a drug or biologically active substance, so as to increase the rate at which the drug or biologically active substance permeates through the membrane. "Permeation enhancer," "enhancer," "penetration enhancer" or similar terms mean a material that achieves such permeation enhancement.

As used herein, "transdermal" means delivery of a drug or biologically active substance by passage into and through the skin or mucosal tissue. Hence, the terms "transdermal" and "transmucosal" are used interchangeably unless specifically stated otherwise. Likewise, the terms "skin," "derma," "epidermis," "mucosa" and the like will also be used interchangeably unless specifically stated otherwise.

As used herein, the term "topical" refers to outer skin or derma of a patient. Hence, the phrase "topical application" refers to the application of a composition of the present invention and its various embodiments to the outer surface of a patient's skin or derma.

As used herein, the terms "occlude," "occluded," "occlusive" and the like refer to a transdermal formulation that is applied to the skin with the use of a supporting or otherwise associated structure. In other words, a topical formulation may be applied to the skin of a patient with the aid of a structure, such as a backing member, bandage or cover. A matrix patch is an example of an occluded device. Conversely, "unoccluded" and "non-occluded," which may be used interchangeably, refer to a transdermal formulation that is applied to the skin without the use of a support, backing member, cover or otherwise associated structure. In other words, the transdermal formulation is applied to the skin in a free form, which is sufficient to effect transdermal delivery of the drug or biologically active substance without the use of structures, such as a backing member, etc. A gel formulation is an example of a non-occluded composition; other non-occluded compositions include ointments, lotions, pastes, mousses, aerosols and creams.

The terms "combination" and "mixture" are used interchangeably and synonymously. These terms should always be interpreted as over-inclusive rather than under-inclusive where appropriate.

Concentration, weight percent and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a percent range of 1% to 20% should be interpreted to include not only the explicitly recited percent limits of 1% and 20% but also to include individual percentages such as 1.5%, 3%, 4.75%, 8.34% and sub-ranges such as 1% to 5%, 10% to 15%, 4.7% to 11.9% etc.

The present invention is a method for treating psoriasis and a composition that is useful for treating psoriasis.

The method comprises the topical application of a composition to the psoriatic area of a patient suffering from a psoriasis outbreak. The composition comprises a sterol ester, preferably a $C_{10}$-$C_{30}$ carboxylic acid sterol ester. The composition may be a gel, cream, paste, lotion, ointment, salve, serum, spray, aerosol, mousse or foam.

The method further comprises the steps of washing the psoriatic area, drying the psoriatic area and optionally exfoliating the psoriatic area prior to the application of the composition. The method or topical application of the composition should occur at least once a day or twice a day directly onto the psoriatic area. Three, 4, 5 or more applications of the composition to the psoriatic area may occur per day depending upon the severity of the psoriasis outbreak and location on the patient's body.

Depending upon the form in which the composition is applied, i.e., gel, serum or cream, after the application of the composition to the psoriatic area, the composition and psoriatic area may be covered with a protective cloth, bandage, gauze or wrap to prevent transfer of the composition to a patient's clothing, furniture or third parties. The protective cloth, bandage, gauze or wrap may also be applied to protect the psoriatic area from dirt, germs and bacteria.

The method of the present invention is repeated every day or portion of the day as needed until the psoriasis outbreak has resided or ended.

The composition of the present invention comprises a sterol ester, preferably a $C_{10}$-$C_{30}$ carboxylic acid sterol ester, and most preferably a $C_{10}$-$C_{30}$ carboxylic acid cholesterol/lanosterol mixture commercially available from Croda Chemicals Europe, Ltd., of East Yorkshire, England under the trade name SUPER STEROL ESTER®. It is believed that $C_{10}$-$C_{30}$ cholesterol/lanosterol ester mixture sold by Croda Chemicals is derived from wool wax by a process described in Koresawa et al., U.S. Pat. No. 4,138,416, which is incorporated in its entirety herein by reference. Additional examples of sterol esters that may be used in the composition of the present invention include but are not limited to stearate, palmitate, acetate, lanolate, macadamiate, nonanoate, oleate, butyrate, hydroxystearate, isostearate, sulfate, isostearate carbonate of cholesterol and other sterols.

The amount of sterol ester in the composition of the present invention should comprise 25% or more of the sterol ester based upon the weight of the composition less solvent, preferably 30% or more based upon the total weight of the composition less solvent and most preferably 40% or more based upon the total weight of the composition less solvent. Because numerous excipients in a transdermal formulation may have the ability to impart multiple functions depending upon the concentration and manner in which they are used, when determining the amount of sterol ester less the amount of solvent present in a composition prepared in accordance with the present invention, the solvents present in the composition but excluded from sterol ester weight percent calculations, are compounds that are liquids at room temperature and have a boiling point below 150° C. under normal atmospheric conditions, preferably a boiling point below 125° C. and most preferably a boiling point below 105° C. Examples of typical solvents that should be excluded from the sterol weight percent calculations are water, low molecular weight alcohols such as $C_1$-$C_6$ branched or straight chain alcohols, e.g., methanol, ethanol and isopropanol, low molecular weight ketones such as $C_1$-$C_6$ branched or straight chain ketones, e.g., acetone, aromatic compounds and low molecular weight alkanes such as $C_1$-$C_{10}$ branched or straight chain alkanes.

The compositions of the present invention may further comprise a penetration enhancer. The amount of penetration enhancer employed in the compositions of the present invention will vary depending upon the specific composition embodiment or transdermal formulation, i.e., serum, cream or foam, and the specific penetration enhancer selected. Typically, the amount of penetration enhancer employed in the compositions of the present invention should be about 0.001 wt % to about 25 wt %, preferably about 0.005 wt % to about 15 wt % and most preferably about 0.01 wt % to about 10 wt % based upon the total weight of the composition. Examples of penetration enhancers that may be used in compositions of the present invention include, but are not limited to, fatty acids, fatty acid esters, fatty alcohols, fatty acid esters of lactic acid or glycolic acid, glycerol tri-, di- and monoesters, triacetin, short chain alcohols, amine oxides and mixtures thereof. Particular examples of permeation enhancers include oleyl alcohol, lauryl alcohol, isopropyl myristate, oleyl oleate, levulinic acid, ethanol, glycerol monooleate, methyl laurate, sorbitain monooleate, triacetin, aloe vera oil, benzothonium chloride, cetyl dimethylamine oxide, cetyl alcohol, cetyl lactate, cocamidopropyl betaine, cocoamine oxide diethanolamine, dimethyloctylamine oxide, 2-dodecoxyethyldimethylamine oxide, dimethyl-decylamine oxide, dimethylhexadecylamine oxide, dim-ethyl-tetradecylamine oxide, dimethyl isosorbide, dipropylene glycol, ethyl hexyl lactate, glycolic acid, 3-dodecoxy-2-hydroxypropyldi(3-hydroxypropyl)amine oxide, lactic acid, lauramine oxide, lauryl betaine, lauryl lactate, lauryl laurate, isopropyl palmitate, macrogol 15 hydroxystearate (Solutol HS 15), menthol, menthyl lactate, myristyl alcohol, myristal lactate, octyldodecanol, octyl salicylate, oleamine oxide, oleic acid, oleyl betaine, oleyldi(2-hydroxyethyl)amine oxide, PEG 1000, pentadecalactone, propylene glycol, salicylic acid, stearyl alcohol, stearyl lactate, 3,6,9-trioxaheptadecyldiethylamine oxide, di(2-hydroxyethyl)-tetradecylamine oxide, triethanolamine triacetate and combinations thereof. Other permeation enhancers useful with the present invention may be found in U.S. Patent Application Publication No. 2007/0269379, which is incorporated in its entirety herein by reference. Preferred permeation enhancers include oleyl alcohol, lauryl alcohol, isopropyl myristate, oleyl oleate, levulinic acid, glycerol monooleate, methyl laurate, sorbitain monooleate, triacetin, cetyl alcohol, cetyl lactate, dimethyl isosorbide, dipropylene glycol, ethyl hexyl lactate, glycolic acid, lauramine oxide, lauryl betaine, lauryl lactate, lauryl laurate, isopropyl palmitate, myristyl alcohol, myristal lactate, octyl salicylate, oleamine oxide, oleic acid, oleyl betaine, salicylic acid, stearyl alcohol, stearyl lactate, triethanolamine triacetate and combinations thereof.

Depending upon the specific composition embodiment or transdermal formulation, i.e., serum, cream or foam, the composition of the present invention may also include further additives such as solvents, film forming/polymeric agents, viscosity increasing agents, emulsifiers, antioxidants, preservatives, pH adjusting agents, propellants and combinations of the forgoing.

The compositions of the present invention may include any suitable solvent. Preferably, the solvent may include water and/or one or more organic compounds, e.g., esters, terpenes, alcohols, ketones, aldehydes, fatty acids, partially or fully esterified fatty acids, wherein the structures are cyclic, non-cyclic (e.g., alkyl), alicyclic (i.e., a bridged ring compound), or aromatic, as well as organic compounds having combinations of these functional groups. Specific examples of solvents that may be employed are water, methanol, ethanol, isopropyl alcohol, acetone, hexane, butyl alcohol, ethyl acetate, polyethylene glycol, propylene glycol, ethylene glycol, triethylene glycol, glycerin, 1,3-propane diol, 2-methyl-1,3-propane diol, glycerol ricinoleate, mineral oil, peanut oil, corn oil, cottonseed oil, sesame oil or a combination thereof. The solvent may be employed in any suitable amount. Typically, the solvent can be present in the composition in about 1.0 wt % to about 95.0 wt % based upon the total weight of the composition, preferably about 3.0 wt % to about 85 wt % based upon the total weight of the composition and most preferably about 5.0 wt % to about 75 wt % of the total weight of the composition.

The compositions of the present invention also may include a film-forming/polymeric agent. Although applicants do not wish to be bound by an particular theory, it is believed that the presence of a film-forming/polymeric agent in the compositions prepared in accordance with the present invention allow the compositions to spread more easily over the skin and to form a protective barrier coating allowing the sterol ester to penetrate the skin of the psoriatic area and/or remain in contact with the skin of the psoriatic area. The film-forming/polymeric agent may also enhance the adherence of the composition to the patient's skin and improve the composition's resistance to wash off or rub off.

Film-forming/polymeric agents are preferably soluble or miscible with the sterol ester and/or penetration enhancer. The composition of the present invention typically comprises from about 0.001 wt % to about 25 wt %, preferably about 0.005 wt % to about 15 wt % and most preferably about 0.010 wt % to about 10 wt % based upon the total weight of the composition. Some examples of film-forming/polymeric agents that may be used in compositions of the present invention are polyalkenes, oleophilic copolymers of vinvylpyrrolidone, acrylic copolymers, polyethylene glycol derivative, polyolefins, polyurethanes and mixtures thereof.

Examples of polyalkenes that may be included in the compositions of the present invention are polyethylenes having a molecular weight ranging from about 300 to about 3000 (available as PERFORMALENE® from New Phase Technologies, Piscataway, N.J.); polyisobutylenes (available as VISTANEX™ from Exxon Chemical Company, Houston, Tex.); polyisobutenes (available as PRESPERSE™ from Sumitomo Corp.); polydecenes (SILKFLO™ available from Amoco); and hydrogenated polyisobutenes (PANALANE® available from Lipo Chemicals, Inc., Paterson, N.J.).

Oleophilic copolymers of vinylpyrollidone suitable for use in the compositions of the present invention may be copolymers of polyvinylpyrrolidone (PVP) and long chain alpha olefins, including, but not limited to, PVP/eicosene copolymers (GANEX® V-220 and V-220F), and tricontanyl PVP copolymers (GANEX®) available from Ashland, formerly International Specialty Products, Wayne, N.J.

Examples of acrylic copolymers that may be used in the compositions of the present invention include acrylic copolymers having long ($C_8$-$C_{30}$) alkyl chains to enhance their oleophilicity, such as acrylate/octylacrylamide copolymers (available as DERMACRYL® from Akzo Nobel). An example of a polyethylene glycol derivative that may be used as a film forming agent in compositions of the present invention is a polyethylene glycol derivative of Beeswax (ESTOL® E04BW-3752, E06BW-3753 or E03BW-3751 formerly available from Unichema, Wilmington, Del. and currently available from Croda under the trade name CITHROL®). Examples of polyolefins that may be used as a film forming agent in compositions of the present invention are fatty acid ester/fatty acid anhydride grafted polyolefins wherein the esters and anhydrides are derived from $C_{12}$-$C_{22}$ fatty acid moieties, for example, $C_{30}$-$C_{38}$ olefin/isopropyl maleate/maleic anhydride copolymer (PERFORMA™ V1608, available from New Phase Technologies, Piscataway, N.J.).

A preferred group of film forming/polymeric agents that may be used in the compositions of the present invention include polyurethanes derived from isophorone di-isocyanate such as those described in U.S. Pat. Nos. 5,051,260 and 6,613,866 and sold by Alzo International Inc. under the tradename POLYDERM®, polyisobutene/polybutene, hydrogenated polydecene and hydrogenated $C_6$-$C_{14}$ olefin polymers sold by ExxonMobil Chemical company under the tradename PURESYN®. The following table identifies a few of the preferred film forming/polymeric agents:

| Commercial Name | Chemical Description | Origin |
| --- | --- | --- |
| POLYDERM ® PPI-BZ | Benzyl Alcohol-Ethylene Glycol/IPDI Copolymer | Alzo International Inc. |
| POLYDERM ® PPI-CA-15 | Di-PEG-15 Cocamine/IPDI Copolymer | Alzo International Inc. |
| POLYDERM ® PPI-CO | Castor Oil/IPDI Copolymer | Alzo International Inc. |
| POLYDERM ® PPI-CO-H | Hydrogenated Castor Oil/IPDI Copolymer | Alzo International Inc. |
| POLYDERM ® PPI-CO-40 | PEG-40 Hydrogenated Castor Oil/IPDI Copolymer | Alzo International Inc. |
| POLYDERM ® PPI-CO-200 | PEG-200 Hydrogenated Castor Oil/IPDI Copolymer | Alzo International Inc. |
| POLYDERM ® PPI-DGDIS | Diglycerol Diisostearate/IPDI Copolymer | Alzo International Inc. |
| POLYDERM ® PPI-GH | Glycereth-7 Hydroxystearate/IPDI Copolymer | Alzo International Inc. |
| POLYDERM ® PPI-PE | Diethylene Glycol Adipate/IPDI Copolymer | Alzo International Inc. |
| POLYDERM ® PPI-SA | Di-2 PEG Soyamine/IPDI Copolymer | Alzo International Inc. |
| POLYDERM ® PPI-SI | Dimethiconol/IPDI Copolymer | Alzo International Inc. |
| POLYDERM ® PPI-SI-50 | Dimethiconol/IPDI Copolymer 50% | Alzo International Inc. |
| POLYDERM ® PPI-SI/SA | Dimethiconol-PEG-2 Soyamine/IPDI Copolymer | Alzo International Inc. |
| POLYDERM ® PPI-SI-WI | Dimethicone Copolyol/IPDI Copolymer water insoluble | Alzo International Inc. |
| POLYDERM ® PPI-SI-WS | Dimethicone Copolyol/IPDI Copolymer water soluble | Alzo International Inc. |
| AVALURE ® UR 450 | PPG-17/IPDI/DMPA Copolymer | Noveon |
| POLYSYNLANE ® Gel | Hydrogenated Polyisobutene (and) Butylene/Ethylene/Styrene Copolymer (and) Ethylene/Propylene/Styrene Copolymer | Collaborative Group |
| POLYFIX ® JPN | Hydrogenated Polyisobutene (and) Polybutene | Collaborative Group |
| POLYSYNLANE ® (HV) | Hydrogenated Polyisobutene | Collaborative Group |
| PANALENE ® H300E | | Lipo Chemicals |
| PANALENE ® L-14E | | Lipo Chemicals |
| PURESYN ® 2, 4, 6, 8, 10, 40, 100, 150, 300 1000, 3000 | Polydecene or Hydrogenated Polydecene | ExxonMobil Chemicals |

The preferred film forming/polymeric agents are water-insoluble, oleophilic and/or water-resistant.

The compositions of the present invention may also contain viscosity enhancing agents that thicken, gel or harden the composition. The composition of the present invention typically comprises from about 0.001 wt % to about 50 wt % of the viscosity enhancing agent, preferably about 0.005 wt % to about 40 wt % and most preferably about 0.01 wt % to about 25 wt % based upon the total weight of the composition. Exemplary viscosity enhancing agents include organic materials such as natural or synthetic waxes, $C_{12}$-$C_{60}$ alcohols, $C_{12}$-$C_{60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Additional viscosity enhancing agents include polyol polyesters, glyceryl esters, polyglyceryl esters and polysiloxanes that are a solid or semi-solid at ambient temperature.

Specific examples of viscosity enhancing agents that may be included in the compositions of the present invention include $C_{12}$-$C_{60}$ alcohols, preferably $C_{16}$-$C_{22}$ fatty alcohols, such as cetyl alcohol, stearyl alcohol, behenyl alcohol and mixtures thereof. Other suitable viscosity enhancing agents include $C_{12}$-$C_{60}$ acids, preferably $C_{16}$-$C_{22}$ fatty acids, such as palmitic acid, stearic acid, behenic acid, oleic acid, linoleic acid, myristic acid, ricinoleic acid, eurcic acid, lauric acid, isostearic acid and mixtures thereof. Further suitable viscosity enhancing agents that may be used herein are alpha-hydroxy fatty acids, including 12-hydroxystearic acid, 12-hydroxylauric acid, 16-hydroxyhexadecanoic acid and mixtures thereof. Additional examples of suitable fatty acids are further described in Klofta et al., U.S. Pat. No. 7,449,613, Hofrichter, et al., U.S. Pat. No. 5,429,816 and Motley, U.S. Pat. No. 5,552,136, disclosure of each is incorporated in its entirety herein by reference.

Waxes are also suitable for use as viscosity enhancing agents in compositions of the present invention. Natural waxes may include, but are not limited to, carnauba, ozokerite, beeswax, candelilla, paraffin, ceresin, esparto, ouricuri, rezowax and other known mined and mineral waxes. Synthetic waxes may include, but are not limited to, paraffin waxes and microcrystalline waxes.

Additional viscosity enhancing agents that may be used herein include polyhydroxy fatty acid esters, polyhydroxy fatty acid amides and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin. Suitable polyhydroxy fatty acid esters and polyhydroxy fatty acid amides are disclosed in Roe et al., U.S. Pat. No. 5,643,588, the disclosure of which is incorporated in its entirety herein by reference.

Still further viscosity enhancing agents that may be included in the compositions of the present invention are gelling agents. Gelling agents are materials that can swell or expand when in contact with water. Examples of gelling agents that may be used in the present invention include swellable polymers, also known as osmopolymers or hydrogels. The swellable polymer can be non-cross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include polyhydroalkylcellulose having a molecular weight greater than 50,000, such as hydroxyl propylmethylcellulose (METHOCEL® K 100M available from Dow Chemical); poly(hydroxyalkylmethacrylate) having a molecular weight of from 5,000 to 5,000,000; poly (vinylpyrrolidone) having a molecular weight of from 100,000 to 3,000,000; anionic and cationic hydrogels; poly (electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams and the like.

Other gelling agents useful in the present invention include pectin having a molecular weight ranging from 30,000 to 300,000; polysaccharides such as agar, acacia, karaya, tragacanth, algins and guar; CARBOPOL®, an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOOD-RITE® polyacrylic acid having a molecular weight of 80,000 to 200,000; POLYOX® polyethylene oxide polymers having a molecular weight of 100,000 to 7,000,000; starch graft copolymers; AQUA-KEEP® acrylate polymers with water absorbability of about 400 times its original weight; diesters of polyglucan; a mixture of cross-linked polyvinyl alcohol and poly(N-vinyl-2-pyrrolidone); poly(ethylene glycol) having a molecular weight of 4,000 to 100,000. Representative polymers possessing gelling properties are described in U.S. Pat. Nos. 6,419,954, 4,915,949, 4,327,725, 4,207,893 and in *Handbook of Common Polymers*, by Scott and Roff, published by Cleveland Rubber Company, Cleveland, Ohio.

Examples of inorganic viscosity enhancing agents that may be included in the compositions of the present invention include treated and untreated fumed silicas such as those available from Cabot Corp., Tuscola, Ill. under the trade designations CAB-O-SIL M5 and MS-55. Exemplary surface-treated fumed silicas are also available from Cabot Corp., Tuscola, Ill. under the trade designations TS-720 and TS-610.

Suitable clays such as hectorite and smectite may also be used as viscosity enhancing agents in compositions of the present invention.

Hydrogenated vegetable oils such as cocoa butter, shea butter and mixtures thereof may also be used as viscosity enhancing agents in compositions of the present invention.

Suitable petroleum-based emollients may also be used as viscosity enhancing agents in compositions of the present invention. Examples of suitable petroleum-based emollients that may be used include petrolatums, i.e., hydrocarbons or mixtures of hydrocarbons; particularly preferred are hydrocarbons having chain lengths of from $C_{10}$ to $C_{100}$. Petroleum-based emollients within this chain length range include mineral oil and petrolatum. Mineral oil usually refers to less viscous mixtures of hydrocarbons having from 10 to 30 carbon atoms, though the hydrocarbon molecular weight distribution may vary. Since the lower molecular weight hydrocarbons can cause irritation in some individuals, mineral oils having a small percentage of lower molecular weight hydrocarbons are preferred. Petrolatum usually refers to more viscous mixtures of hydrocarbons of higher molecular weight hydrocarbons. Petrolatum and mineral oil are preferred skin conditioning agents for compositions of the present invention due to their ability to protect the skin from harmful or irritating stimuli. Petrolatum is particularly preferred because of its good barrier properties.

The compositions of the present invention may also contain humectants. The compositions of the present invention typically comprises from about 0.001 wt % to about 30 wt % of a humectant, preferably about 0.005 wt % to about 20 wt % and most preferably about 0.01 wt % to about 10 wt % based upon the total weight of the composition. Examples of compounds that may be used as humectants in compositions of the present invention are esters of polyhydroxy alcohols. This type of ester may include glyceryl esters including glycerides and derivatized glycerides, polyglyceryl esters, and glycolic esters. Glyceryl esters are derived from glycerin, its derivatives and one or more carboxylic acid moieties. Non-limiting examples include various $C_1$-$C_{30}$ mono-, di- or tri-esters of glycerin and derivatives thereof, such as mono-, di-, tri-glycerides, acetoglycerides, and ethoxylated glycerides. Exemplary glyceryl esters include glyceryl behenate, glyceryl oleate, glyceryl stearate, glyceryl palmitate, glyceryl distearate, glyceryl dipalmitate and the like. Polyglyceryl esters having $C_{12}$-$C_{22}$ acid moieties are also suitable for use herein. Non-limiting examples include polyglyceryl-4 isostearate, polyglyceryl-3 oleate, diglyceryl monooleate, tetraglyceryl monooleate and the like. Glycolic esters are derived from $C_2$-$C_6$ glycols, including ethylene glycol, propylene glycol, butylene glycol, hexylene glycol and derivatives thereof, and one or more carboxylic acid moieties having $C_1$-$C_{30}$ chains. Specific examples of glycolic esters include polyethylene glycols (PEGs), such as PEG-2, PEG-3, PEG-30 and PEG-50, and polypropylene glycols (PPGs), such as PPG-9, PPG-12, PPG-15, PPG-17, PPG-20, PPG-26, PPG-30 and PPG-34.

The compositions of the present invention may also contain emulsifiers or dispersing agents such as anionic, cationic and nonionic surfactants. The compositions of the present invention typically comprises from about 0.001 wt % to about 15 wt % of an emulsifier or dispersing agent, preferably about 0.005 wt % to about 10 wt % and most preferably about 0.01 wt % to about 5 wt % based upon the total weight of the composition. Nonionic surfactants are preferred because of their low level of irritation to skin. Typical nonionic surfactants are monoglycerides such as glyceryl monostearate and the like; sorbitan aliphatic esters such as sorbitan monolaurate and the like; sucrose aliphatic esters; polyoxyethylene aliphatic esters such as polyoxyethylene stearate; and polyoxyethylene higher alcohol ethers such as polyoxyethylene cetyl ether, polyoxyethylene oleyl ether, polyoxyethylene fatty ethers and the like.

The compositions of the present invention may also contain an antioxidant to minimize or prevent the oxidation process and enhance the shelf life of the composition. The compositions of the present invention typically comprises from about 0.001 wt % to about 25 wt % of an anti-oxidant, preferably about 0.005 wt % to about 15 wt % and most preferably about 0.01 wt % to about 10 wt % based upon the total weight of the composition. Antioxidants useful herein should preferably be mild and non-irritating. Antioxidants from natural sources are preferred, such as Vitamin E and its derivatives, including tocopherol, tocopherol acetate, mixed tocopherols (available as COVI-OX T-50 or T-70 from Henkel Corp, Ambler, Pa.), and the like or butylated hydroxytoluene, butylated hydroxyanisole, sodium pyrosulfite, acetone sodium bisulfate and the like. Some of these antioxidants are also useful as skin antioxidants, which minimizes the wrinkles and dullness of the skin and provides a more youthful looking and firmer textured skin.

The compositions of the present invention may also contain a preservative to prevent bacterial growth and odors thereof, particularly in compositions having a relatively high water content. The compositions of the present invention typically comprise from about 0.001 wt % to about 10 wt % of a preservative, preferably about 0.005 wt % to about 5 wt % and most preferably about 0.01 wt % to about 2.5 wt % based upon the total weight of the composition. Suitable preservatives include propyl paraben, methyl paraben, benzyl alcohol, benzalkonium chloride, tribasic calcium phosphate, phenoxyethanol, or acids such as citric, tartaric, maleic, lactic, malic, benzoic, salicylic and the like.

The compositions of the present invention may include an acid or base to adjust the pH of the composition to the desired or optimal range. Examples of compounds typically used to adjust the pH of topical compositions include oleic acid, hydrochloric acid, citric acid, lactic acid, tartaric acid, glacial acetic acid, sodium hydroxide or the like. Depending upon the form in which the composition is applied, i.e., gel, serum or cream, and the location, the desired final pH value of the composition may vary, however, it is generally preferred that the composition range from a pH of about 5.0 to about 8.5, preferably about 6 to about 8.0 and most preferably about 6.5 to about 7.5.

In order to increase the stability of the compositions of the present invention, it may be necessary to add a chelating agent. The chelating agents may include ethylenediaminetetraacetic acid (EDTA) and its derivatives, thioglycolic acid, thiolactic acid, thioglycerol and the like.

A fragrance may also be added to composition of the present invention if desired.

If the composition of the present invention is an aerosol, foam or mouse, the composition will require a propellant for dispensing the composition from the container. The propellant may be any type of propellant commonly used in the cosmetic/pharmaceutical industry such as nitrogen, carbon dioxide, dimethyl ether, hydrocarbons, i.e., methane, ethane, propane, butanes and pentanes, halogenated hydrocarbons, i.e., $CH_2ClF$, $CClF_2CHClF$, $CF_3CHClF$, $CHF_2CClF_2$, $CHClFCHF_2$, $CF_3CH_2C_1$, $CClF_2CH_3$, $CHF_2CHF_2$, $CF_3CH_2F$ (HFC 134a), $CHF_2CH_3$ (HFC 152a), $CF_3CHFCF_3$ (HFC 227), $CF_3CF_3$ and $CF_3CF_2CF_3$. Some of the more commonly used hydrocarbon propellants are A-46 (15.2% propane/84.8% isobutene); and NP-46 (25.9% propane/74.1% n-butane), NIP-46 (21.9% propane/31.3% isobutene/46.8% n-butane). The amount of propellant will depend on the type of container for the composition of the present invention, the amount of the composition in the container, the amount of composition to be dispensed per actuation and the form in which the composition will be dispensed, i.e., mist or foam. The optimization of the propellant and container are within the ability of the skilled artisan and examples can be found in Wai-Chiu So et al., U.S. Pat. No. 6,946,120 and Remington, Science and Practice of Pharmacy, $21^{st}$ ed., pp. 1000-1017 which are incorporated in their entirety herein by reference. The propellant is generally not included in the calculation of the weight percentages of the composition prepared in accordance with the present invention because it is merely part of the dispensing device and typically does not remain part of the composition once the composition is dispensed and applied to the patient's psoriatic area.

The aerosols, foams and mousses of the present invention will include a solvent, preferably water and/or a lower alcohol, i.e., $C_1$-$C_6$ alcohols such as methanol, ethanol, isopropanol or mixtures thereof. The aerosols, foams or mousses may also comprise a co-solvent selected from one or more of the group consisting of aromatic and polyhydric alcohols such as 1,3-butylene glycol, propylene glycol, polyethylene glycol 400, hexylene glycol and dipropylene glycol or glycerol. When the co-solvent is present, it may be present in amounts of approximately 10% by weight or less, preferably approximately 5% by weight or less based upon the total weight of the composition.

The composition of the present invention may also include an anti-inflammatory drug, a topical anesthetic or a combination thereof. Typical topical anesthetics include, but are not limited to, lidocaine, xylocaine, buprenorphine and fentanyl. Suitable topical anesthetics are known to those of skill in the art and are disclosed, e.g., in Goodman Gilman, Alfred; Goodman, Louis S.; Gilman, Alfred; Goodman and Gilman's The Pharmacological Basis of Therapeutics, Ninth Edition, pp. 331-347.

Any suitable topical corticosteroid can be employed as an anti-inflammatory drug. Suitable corticosteroids are known to those of skill in the art and are disclosed in, e.g., Goodman Gilman, Alfred; Goodman, Louis S.; Gilman, Alfred; Goodman and Gilman's The Pharmacological Basis of Therapeutics, Ninth Edition, pp. 1459-1483. Suitable exemplary corticosteroids include cortisol (hydrocortisone); tetrahydrocortisol; prednisone (cortisone); prednisolone (cortisol); 6α-methylprednisolone; fludrocortisone (9α-fluorocortisol); 11-desoxycortisol; cortisone (11-dehydrocortisol); corticosterone; triamcinolone (9α-fluoro-16α-hydroxyprednisolone); paramethasone (6α-fluoro-16α-methylprednisolone); betamethasone (9α-fluoro-16β-methylprednisolone); dexamethasone (9α-fluoro-16α-methylprednisolone); desoxycorticosterone acetate (doca acetate, percorten acetate); desoxycorticosterone pivalate (percorten pivalate); fludrocortisone acetate (florine acetate); cortisol (hydrocortisone) (cortef, hydrocortone); cortisol acetate (cortef acetate, hydrocortone acetate); cortisol cypionate (cortef); cortisol sodium phosphate (hydrocortone phosphate); cortisol sodium succinate (solu-cortef); beclopmethasone dipropionate (vanceril); betamethasone (celestone); betamethasone sodium phosphate and acetate (celestone soluspan); betamethasone dipropionate (diprosone); betamethasone valerate (valisone); betamethasone benzoate (benisone, flurodate); cortisone acetate (cortone acetate); dexamethasone (decadron, gammacorten); dexamethasone sodium phosphate (decadron phosphate, hexadrol phosphate); dexamethasone acetate (decadron-L.A.); fuprednisolone (alphadrol); meprednisone (betapar); methylprednisolone (medrol); methylprednisolone acetate (depo-medrol, medrol acetate); methylprednisolone sodium succinate (solu-medrol); paramethasone acetate (haldrone); prednisolone (delta-cortef); prednisolone acetate (meticortelone acetate); prednisolone sodium phosphate (hydeltrasol); prednisolone sodium succinate (meticortelone soluble); prednisolone tebutate (hydelta-T.B.A.); prednisone (deltasone, paracort); triamcinolone (aristocort, kenacort); triamcinolone acetonide (aristoderm, kenalog); triamcinolone diacetate (aristocort diacetate, kienacort diacetate); triamcinolone hexacotonide (aristospan); desonide (tridesilon); desoximetasone (topicort); flumethasone pivalate (locorten); fluocinolone acetonide (fluonid, synalar); fluocinonide (lidex, topsyn); fluorometholone (oxylone); flurandrenolide (cordran); halcinonide (halog); and medrysone (HMS liqui-film, medrocort).

Preferably, the amount of a suitable topical anti-inflammatory or topical anesthetic can be present in about 0.1 wt % to about 99.9 wt % of the composition. Typically, the amount of anesthetic and/or anti-inflammatory present will depend upon the specific anesthetic and anti-inflammatory employed in the composition. In some embodiments of the present invention, the anesthetic and/or anti-inflammatory can be up to about 10 wt %, up to about 5 wt %, up to about 2 wt %, up to about 1 wt % or up to about 0.1 wt % of the composition. Additionally, the nature and amount of the anesthetic and/or anti-inflammatory present in the composition should comply with any State and/or Federal guidelines that regulate the use of such compounds (e.g., FDA regulations).

The compositions of the present invention may also include known psoriasis treatment agents such as anthralin, also known as dithranol, vitamin D such as calcipotriene or calcitriol, and vitamin A such as tazarotene. Some of the known psoriasis treatment agents are described in greater detail in Goodman Gilman, Alfred; Goodman, Louis S.; Gilman, Alfred; Goodman and Gilman's The Pharmacological Basis of Therapeutics, Ninth Edition, pp. 1591-1613.

The following tables provide a summary overview of a few representative compositions that can be prepared in accordance with the present invention and is not intended to limit the present invention:

Serum

| Ingredient | Preferred Weight % | Most Preferred Weight % |
|---|---|---|
| Sterol Ester | 75-99% | 80-95% |
| Penetration Enhancer | 0.01-15% | 0.1-10% |
| Film-Forming/Polymeric Agent | 0.1-10% | 0.5-5% |
| Antioxidant | 0-10% | 0.5-5% |
| Preservative | 0-10% | 0.5-5% |
| Vitamin(s) | 0-25% | 0-15% |

Salve

| Ingredient | Preferred Weight % | Most Preferred Weight % |
|---|---|---|
| Sterol Ester | 40-90% | 60-85% |
| Penetration Enhancer | 0.01-15% | 0.1-10% |
| Film-Forming/Polymeric Agent | 0.1-10% | 0.5-5% |
| Viscosity Enhancing Agent | 5-40% | 10-25% |
| Antioxidant | 0-10% | 0.5-5% |
| Preservative | 0-10% | 0.5-5% |
| Vitamin(s) | 0-25% | 0-15% |

Cream/Lotion/Gel

| Ingredient | Preferred Weight % | Most Preferred Weight % |
|---|---|---|
| Sterol Ester | (30-80%)* | (40-70%)* |
| Penetration Enhancer | 0.01-15% | 0.1-10% |
| Film-Forming/Polymeric Agent | 0.1-10% | 0.5-5% |
| Viscosity Enhancing Agent | 1-40% | 3-20% |
| Solvent | 5-85% | 10-75% |
| Emulsifier | 0.1-20% | 1-10% |
| Antioxidant | 0-10% | 0.5-5% |
| Preservative | 0-10% | 0.5-5% |

*weight percent based upon amount of sterol ester less solvent

Aerosol/Mousse/Foam

| Ingredient | Preferred Weight % | Most Preferred Weight % |
|---|---|---|
| Sterol Ester | (30-75%)* | (35-60%)* |
| Penetration Enhancer | 0.001-10% | 0.002-5% |
| Film-Forming/Polymeric Agent | 0.001-10% | 0.005-5% |
| Viscosity Enhancing Agent | 0.001-30% | 0.005-20% |
| Solvent | 50-95% | 60-90% |
| Emulsifier | 0.1-20% | 1-10% |
| Propellant | 0.5-25% | 1-10% |
| Antioxidant | 0-10% | 0.001-5% |
| Preservative | 0-10% | 0.001-5% |

*weight percent based upon amount of sterol ester less solvent

EXAMPLES

The following are provided by way of example only and are by no means intended to be limiting.

Example 1

A serum with the following composition is prepared:

| | |
|---|---|
| SUPER STEROL LIQUID | 91.5 wt % |
| Shea Butter | 1.0 wt % |
| Lauryl Laurate | 2.5 wt % |
| POLYDERM PPI-SA | 1.0 wt % |
| Oleic Acid | 1.0 wt % |
| Vitamin-A Palmitate | 1.0 wt % |
| Vitamin -E Acetate | 1.0 wt % |
| Phenoxyethanol | 1.0 wt % |

The serum is prepared by adding the SUPER STEROL LIQUID, shea butter, POLYDERM PPI-SA, oleic acid and lauryl laurate to a suitable mixer and heating the mixture at 75-85° C. for about 30 minutes until a clear solution is obtained. The SUPER STEROL LIQUID is commercially available from Croda Chemicals Europe, Ltd., of East Yorkshire, England and is a mixture of $C_{10}$-$C_{30}$ cholesterol and lanosterol esters. POLYDERM PPI-SA is a Di-PEG-2 Soyamine/IPDI copolymer commercially available from Alzo International Inc.

The resulting composition is removed from the heat and the stirring is continued. Once the temperature of the composition is 50° C. or lower, vitamin A palmitate, vitamin E acetate and phenoxyethanol are added to the composition while stirring is maintained. Once the composition obtains room temperature, the serum composition is packaged in a pump bottle.

Example 2

A salve with the following composition is prepared:

| | |
|---|---|
| SUPER STEROL SOLID | 75 wt % |
| Shea Butter | 15 wt % |
| Lauryl Laurate | 2.5 wt % |
| POLYDERM PPI-SA | 2.5 wt % |
| Oleic Acid | 1.0 wt % |
| Vitamin-A Palmitate | 1.5 wt % |
| Vitamin -E Acetate | 1.5 wt % |
| Phenoxyethanol | 1.0 wt % |

The above salve is prepared by mixing the above ingredients in a suitable mixer by the procedure outlined in Example 1 and filling the slave into a suitable tube for dispensing by the patient.

Example 3

A cream is with the following composition is prepared:

| | |
|---|---|
| SUPER STEROL LIQUID | 18.3* wt % |
| Shea Butter | 0.2 wt % |
| Lauryl Laurate | 0.5 wt % |
| POLYDERM PPI-SA | 0.2 wt % |
| Oleic Acid | 0.2 wt % |
| Vitamin-A Palmitate | 0.2 wt % |
| Vitamin -E Acetate | 0.2 wt % |
| Phenoxyethanol | 0.2 wt % |
| POLAWAX ™ | 10.0 wt % |
| Water | 68.5 wt % |
| Cetyl Alcohol | 1.4 wt % |
| DOWICIL ™-200 | 0.1 wt % |

*58.1% less the solvent (water)

The cream is prepared by adding the serum of Example 1, the POLAWAX™ water and cetyl alcohol to a suitable mixer and heating the mixture at 75-85° C. for about 20-30 minutes. POLAWAX™ is a higher fatty alcohol self-emulsifying wax commercially available from Croda Chemicals Europe, Ltd., of East Yorkshire, England. DOWICIL™-200 is a 1-3-chloroallyl-3,5,7-triaza-1-azoniaadamantane chloride preservative/anti-microbial compound commercially available from Dow Chemical Co. The resulting composition is removed from the heat and the stirring is continued. Once the solution obtains room temperature, the DOWICIL™-200 is added and the cream is packaged in a tube, jar, bottle or other suitable container.

Example 4

A foam with the following composition is prepared:

| | |
|---|---|
| SUPER STEROL LIQUID | 9.15* wt % |
| Shea Butter | 0.01 wt % |
| Lauryl Laurate | 0.025 wt % |
| POLYDERM PPI-SA | 0.01 wt % |
| Oleic Acid | 0.01 wt % |
| Vitamin-A Palmitate | 0.01 wt % |
| Vitamin -E Acetate | 0.01 wt % |
| Phenoxyethanol | 0.01 wt % |
| Glycerox 767 | 10.0 wt % |
| Water | 80.0 wt % |

*45.75% less solvent (water

The above foam composition is prepared by adding the serum of Example 1, GLYCEROX 767 and water to a suitable mixer and heating the mixture at 75° C. for about 10 minutes. GLYCEROX 767 is a PEG-6 capric/caprylic glycerides commercially available from Croda Chemicals Europe, Ltd., of East Yorkshire, England. The resulting composition is removed from the heat and stirred until it obtains room temperature. The composition is filled into a sealed aerosol container along with A-46 propellant (15.2% propane/84.8% isobutene) commercially available from Diversified CPC International. The final aerosol container comprises approximately 96.5% of the above foam composition and 3.5% of the propellant with a pressure of about 46 PSIG @ 75° F.

Example 5

The serum prepared in Example 1 was applied 14 patients suffering from psoriasis. The treatment regimen and results are summarized in the TABLE 1.

TABLE 1

| Subject | Age | Sex | Affected Area | Tx Duration | Tx | Previous Treatment | Result |
|---|---|---|---|---|---|---|---|
| 01 | 13 y.o. | F | right knee behind right knee behind left knee | 1 day | One treatment | AQUAPHOR ® (OTC) used for dry skin hydrocortisone 1% | Complete resolution. |
| 02 | 41 y.o. | M | upper back lower back chest small area on face stomach. | 10 months | Pt. applied serum, exfoliator, and wash 3x/wk at home University to try the serum. | Pt. declined monoclonal antibody tx at Mayo Clinic and other options at the Rockefeller | Pt. recovered 100% but still has residual pre-existing scars. |

TABLE 1-continued

| Subject | Age | Sex | Affected Area | Tx Duration | Tx | Previous Treatment | Result |
|---|---|---|---|---|---|---|---|
| 03 | 41 y.o. | M | left forearm left elbow left wrist left hand right forearm stomach back of leg | 14 months | Pt. applied serum everyday at home in addition to application on each clinical visit | Pt. declined i.v. clinical trial tx at Mayo Clinic to try the serum. | Left and right forearm, left hand, and back of right leg improved 100%. Stomach, left wrist and left elbow improved 30-40%. |
| 04 | 56 y.o. | M | left knee right knee back of right foot | 1 day | One treatment | none | Complete resolution. |
| 05 | 46 y.o. | M | left knee | 1 day | One treatment | coco butter | Complete resolution. |
| 06 | Tx at 6 m.o. | M | right foot right leg left foot left leg left buttock | 1 day | One treatment | ocean salt water | Complete resolution. |
| 07 | 33 y.o. | M | right ankle left arm near elbow | 1 month | Applied serum 1x/day | none | Complete resolution of symptoms. Partial resolution of physical appearance of lesions. |
| 08 | 56 y.o. | F | left hand left wrist left forearm left elbow right hand right wrist right elbow heel of left foot heel of right foot bottom of left foot | 7 months | Applied serum 1x/day | HUMIRA ® SORIATANE ® light therapy laser treatment | 80-100% resolution involving all lesions. |
| 09 | 63 y.o. | M | left knee left forearm near elbow right knee right forearm near elbow | 6 months | Applied serum 1x/day | none | 90-100% resolution involving all lesions. |
| 10 | 53 y.o. | F | left knuckles left elbow left ankle | 1 day | One treatment | VASELINE ® | Reported benefit, however, pt. was unable to follow-up due to |

TABLE 1-continued

| Subject | Age | Sex | Affected Area | Tx Duration | Tx | Previous Treatment | Result |
|---|---|---|---|---|---|---|---|
| | | | right knuckles right elbow | | | | transportation issues. |
| 11 | 60 y.o. | F | left hand left arm left foot left ankle left leg right hand right arm right foot right ankle right leg upper back lower back | 1 day | One treatment | topical triamcinolone acetonide 0.1% 2x/day steroid injections prednisone topical corticosteroid lotion | 80% resolution. |
| 12 | 39 y.o. | F | right elbow right arm right knee right shin left elbow left forearm near elbow left knee left shin stomach | 3 weeks | Applied serum 1x/day for 3 wks | artificial tanning with UV lights | 80% resolution of symptoms. 50% resolution of physical appearance. |
| 13 | 48 y.o. | M | facial | 3-6 months | Applied serum 1x/day | none | Complete resolution. |
| 14 | 37 y.o. | M | upper torso/neck | 1-3 months | Applied serum 1x/day | none | Complete resolution. |

Example 6

One male patient has reported relief of sunburn pain after a single application of the serum prepared in Example 1. The serum was applied to the sunburnt area in the evening prior to bedtime and the patient reported relief when he awoke in the morning.

While certain preferred and alternative embodiments of the present invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

All documents, patents and other literature referred to herein are incorporated by reference in their entirety.

The term "comprising" as used in the following claims is an open-ended transitional term that is intended to include additional elements not specifically recited in the claims. The term "consisting essentially of" as used in the following claims is a partially closed transitional phrase and is intended to include the recited elements plus any unspecified elements that do not materially affect the basic and novel characteristics of the claims. For example, an adhesive laminate (the outermost layer of the applied patch) embossed or printed with indicia would still be included in the meaning of "consisting essentially of", even if not specifically recited. The term "consisting of" as used in the following claims is intended to indicate that the claims are restricted to the recited elements.

It should be noted that it is envisioned that any feature or element that is positively identified in this document may also be specifically excluded as a feature or element of an embodiment of the present invention.

The invention claimed is:

1. A topical composition comprising:
   (a) about 75 wt % to about 99 wt % of a $C_{10}$-$C_{30}$ carboxylic acid cholesterol/lanosterol mixture;
   (b) about 0.01 wt % to about 15 wt % of a combination of penetration enhancers comprising lauryl laurate and a penetration enhancer selected from the group consisting of oleyl alcohol, lauryl alcohol, isopropyl myristate, oleyl oleate, levulinic acid, glycerol monooleate, methyl laurate, sorbitan monooleate, triacetin, cetyl alcohol, cetyl lactate, dimethyl isosorbide, dipropylene glycol, ethyl hexyl lactate, glycolic acid, lauramine oxide, lauryl betaine, lauryl lactate, isopropyl palmitate, myristyl alcohol, myristal lactate, octyl salicylate, oleamine oxide, oleic acid, oleyl betaine, salicylic acid, stearyl alcohol, stearyl lactate, triethanolamine triacetate, and combinations thereof;
   (c) about 0.1 wt % to about 10 wt % of a film forming polymeric agent;
   (d) about 0.005 wt % to about 40 wt % of a viscosity increasing agent selected from the group consisting of natural waxes, synthetic waxes, gelling agents, fumed silicas, clays, hydrogenated vegetable oils, petrolatums and mixtures thereof;

(e) 0 to about 10 wt % of an antioxidant; and (f) 0 to about 10 wt % of a preservative.

2. The topical composition of claim 1 wherein the combination of penetration enhancers comprises lauryl laurate, oleic acid, and salicylic acid.

3. The topical composition of claim 1 wherein the film forming polymeric agent comprises a water insoluble film forming polymeric agent.

4. The topical composition of claim 1 wherein the film-forming polymeric agent is selected from the group consisting of polyalkenes, oleophilic copolymers of vinylpyrrolidone, acrylic copolymers, polyethylene glycol derivatives, polyolefins, polyurethanes, and mixtures thereof.

5. The topical composition of claim 1 wherein the carboxylic acid cholesterol/lanosterol mixture comprises about 75 wt % to about 95 wt % of the topical composition.

6. The topical composition of claim 1 wherein the carboxylic acid cholesterol/lanosterol mixture comprises about 80 wt % to about 95 wt % of the topical composition.

7. The topical composition of claim 1 wherein the film forming polymeric agent comprises a polyurethane.

8. The topical composition of claim 1 wherein the viscosity increasing agent comprises a hydrogenated vegetable oil.

9. A topical composition comprising:

(a) about 75 wt % to about 99 wt % of a $C_{10}$-$C_{30}$ carboxylic acid cholesterol/lanosterol mixture;

(b) about 0.01 wt % to about 15 wt % of a combination of lauryl laurate, oleic acid and salicylic acid;

(c) about 0.1 wt % to about 10 wt % of a water insoluble film forming polymeric agent;

(d) about 0.005 wt % to about 40 wt % of a viscosity increasing agent selected from the group consisting of natural waxes, synthetic waxes, gelling agents, fumed silicas, clays, hydrogenated vegetable oils, petrolatums and mixtures thereof;

(e) 0 to about 10 wt % of an antioxidant; and (f) 0 to about 10 wt % of a preservative.

10. The topical composition of claim 9 wherein the carboxylic acid cholesterol/lanosterol mixture comprises about 75 wt % to about 95 wt % of the topical composition.

11. The topical composition of claim 9 wherein the carboxylic acid cholesterol/lanosterol mixture comprises about 80 wt % to about 95 wt % of the topical composition.

12. The topical composition of claim 9 wherein the film forming polymeric agent comprises a polyurethane.

13. The topical composition of claim 9 wherein the viscosity increasing agent comprises a hydrogenated vegetable oil.

14. The topical composition of claim 9 comprising about 0.5 wt % to about 5 wt % of an antioxidant wherein the antioxidant comprises an antioxidant selected from the group consisting of Vitamin E, tocopherol, tocopherol acetate and mixed tocopherols.

15. The topical composition of claim 9 wherein the topical composition further comprises 0 to about 15 wt % of a vitamin A.

16. The topical composition of claim 15 wherein the vitamin A comprises tazarotene or vitamin A palmitate.

17. A topical composition consisting of:

(a) about 75 wt % to about 95 wt % of a $C_{10}$-$C_{30}$ carboxylic acid cholesterol/lanosterol mixture;

(b) about 0.1 wt % to about 10 wt % of lauryl laurate, oleic acid, salicylic acid or a combination thereof;

(c) about 0.1 wt % to about 10 wt % of a film forming polymeric agent;

(d) about 0.005 wt % to about 40 wt % of a viscosity increasing agent wherein the viscosity increasing agent selected from the group consisting of natural waxes, synthetic waxes, gelling agents, fumed silicas, clays, hydrogenated vegetable oils, petrolatums and mixtures thereof;

(e) 0 to about 10 wt % of an antioxidant;

(f) 0 to about 10 wt % of a preservative; and (g) 0 to about 15 wt % of a vitamin A.

\* \* \* \* \*